United States Patent [19]

Yamada et al.

[11] Patent Number: 5,789,211
[45] Date of Patent: *Aug. 4, 1998

[54] GENE ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

[75] Inventors: Hideaki Yamada, 19-1, Matsugasaki Kinomotocho, Sakyo-ku, Kyoto-fu, Kyoto-shi; Toru Nagasawa, Kyoto; Teruhiko Beppu, 5-21, Horinouchi 1-chome, Suginami-ku, Tokyo; Sueharu Horinouch; Makoto Nishiyama, both of Tokyo, all of Japan

[73] Assignees: Nitto Chemical Industry Co., Ltd.; Teruhiko Beppu; Hideaki Yamada, all of, Japan

[*] Notice: The term of this patent shall not extend beyond the expiration date of Pat. No. 5,648,256.

[21] Appl. No.: 463,470

[22] Filed: Jun. 5, 1995

Related U.S. Application Data

[63] Continuation of Ser. No. 233,146, Apr. 22, 1994, Pat. No. 5,648,256, which is a continuation of Ser. No. 694,746, May 2, 1991, abandoned.

[51] Int. Cl.$^6$ .............. C12P 13/02; C12N 1/00; C12N 9/88; C12N 15/60; C12N 15/63
[52] U.S. Cl. .............. 435/129; 435/232; 435/320.1; 435/252.3; 435/254.11; 536/23.2
[58] Field of Search ................ 435/232, 252.3, 435/252.33, 254.11, 240.1, 320.1, 129, 227; 530/23.2

[56] References Cited

U.S. PATENT DOCUMENTS 5,648,256  7/1997  Yamada et al. ............ 435/232

OTHER PUBLICATIONS

Hashimoto et al., 1991, Biochim. Biophys Acta 1088(2): 225–233.
Nagasawa et al., 1988, Biochim. Biophys. Res. Commun. 155(2): 1008–1016.
Ikehata et al., 1989, Eur. J. Biochem. 181(3): 563–570.
Abstract entitled Purification and Characterization of Nitrile Hydratase Produced by *Rhodococcus rhodochrous* J. Nagasawa et al., 1988, Seikagaku vol. 60(8), p. 647, 1988, and Applicants' translation thereof.
Nagasawa et al., 1987, Eur. J. Biochem., 162:691–698.
Asano et al., 1982, Agric. Biol. Chem., 46(5), 1183–1189.
Yamada, 1986, Agric. Biol. CHem., 50(11), 2859–2865.
Nishiyama et al., 1991, J. Bacteriol, (Apr. 1991) 173(8): 2465–72.
Abstract entitled "2Xa3 Cloning and Structure Analysis of a Nitrilhydratase (NHase) Gene of *Pseudomonas chlororaphis* B23" by Nishiyama et al., 1990 (Mar. 1990) 64(03) Nippon Nogeikagaku Kaishi and Applicants' translation thereof.
Abstract entitled "2Xp3 Cloning of Two Types of Nitrilhydratase (NHase) Genes Derived from *Rhodococcus rhodochrous*" by Kobayshi et al., 1990, (Mar., 1990) 64(03) Nippon Nogeikagaku Kaishi and Applicants' translation thereof.

(List continued on next page.)

*Primary Examiner*—Charles L. Patterson, Jr.
*Assistant Examiner*—Gabriele E. Bugaisky
*Attorney, Agent, or Firm*—Pennie & Edmonds LLP

[57] ABSTRACT

The present invention relates to a gene derived from *Pseudomonas chlororaphis* B23 strain which encodes a polypeptide having nitrile hydratase activity being capable of hydrating nitriles to amides. The invention also relates to a recombinant DNA containing the gene, and a transformant transformed with the recombinant DNA. The present invention further relates to a method of producing nitrile hydratase using the transformant and of amides using nitrile hydratase.

8 Claims, 1 Drawing Sheet

OTHER PUBLICATIONS

Ikehata et al., 1988, Lecture Summary, Japan Soc. for Fermentation, p. 22.

Abstract entitled "2Xo2 Cloning of the Amidase Gene of *Rhodococcus* sp. N–774 and Expression of the Gene in *E. coli*" by Hashimato et al., 1990 (Mar., 1990) 64(03) Nippon Nogeikagaku Kaishi and Applicants' translation thereof.

Nagasawa et al., Jul., 1990, Yuki Gosei Kagaku Kyoskaishi 48(11): 1072–73.

Hjort et al., 1990, (Mar. 20, 1990) J. Chem. Technol. 48(11): 1072–73.

Yamada et al., 1990, Ann. N.Y. Acad. Sci., Dec. 28, 1990, 613: 142–154.

Mayaux et al., 1990, J. Bacteriol., Dec., 1990, 172(12): 6764–73.

Sun et al., 1990, Gongye Weishengwu, 1990 20(3): 18–20.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Pseudomonas chlororaphis
        ( B ) STRAIN: B23 (FERM BP-187)

( x i ) SEQUENCE DESCRIPTION: SEQ ID NO:1:

```
Met Ser Thr Ser Ile Ser Thr Thr Ala Thr Pro Ser Thr Pro Gly Glu
 1               5                  10                  15

Arg Ala Trp Ala Leu Phe Gln Val Leu Lys Ser Lys Glu Leu Ile Pro
            20                  25                  30

Glu Gly Tyr Val Glu Gln Leu Thr Gln Leu Met Ala His Asp Trp Ser
        35                  40                  45

Pro Glu Asn Gly Ala Arg Val Val Ala Lys Ala Trp Val Asp Pro Gln
    50                  55                  60

Phe Arg Ala Leu Leu Leu Lys Asp Gly Thr Ala Ala Cys Ala Gln Phe
65                  70                  75                  80

Gly Tyr Thr Gly Pro Gln Gly Glu Tyr Ile Val Ala Leu Glu Asp Thr
                85                  90                  95

Pro Gly Val Lys Asn Val Ile Val Cys Ser Leu Cys Ser Cys Thr Asn
            100                 105                 110

Trp Pro Val Leu Gly Leu Pro Pro Glu Trp Tyr Lys Gly Phe Glu Phe
        115                 120                 125
```

```
    Arg  Ala  Arg  Leu  Val  Arg  Glu  Gly  Arg  Thr  Val  Leu  Arg  Glu  Leu  Gly
         130                     135                     140

Thr  Glu  Leu  Pro  Ser  Asp  Thr  Val  Ile  Lys  Val  Trp  Asp  Thr  Ser  Ala
    145                          150                     155                      160

Glu  Ser  Arg  Tyr  Leu  Val  Leu  Pro  Gln  Arg  Pro  Glu  Gly  Ser  Glu  His
                        165                     170                     175

Met  Ser  Glu  Glu  Gln  Leu  Gln  Gln  Leu  Val  Thr  Lys  Asp  Val  Leu  Ile
                   180                     185                     190

Gly  Val  Ala  Leu  Pro  Arg  Val  Gly
                   195                200
```

( 2 ) INFORMATION FOR SEQ ID NO:2:

( i ) SEQUENCE CHARACTERISTICS:
        ( A ) LENGTH: 220 amino acids
        ( B ) TYPE: amino acid
        ( C ) STRANDEDNESS: single
        ( D ) TOPOLOGY: linear     ( i i ) MOLECULE TYPE: peptide     ( v i ) ORIGINAL SOURCE:
        ( A ) ORGANISM: Pseudomonas chlororaphis
        ( B ) STRAIN: B23 (FERM BP-187)

( x i ) SEQUENCE DESCRIPTION: SEQ ID NO:2:

```
    Met  Asp  Gly  Phe  His  Asp  Leu  Gly  Gly  Phe  Gln  Gly  Phe  Gly  Lys  Val
    1                   5                        10                      15

Pro  His  Thr  Ile  Asn  Ser  Leu  Ser  Tyr  Lys  Gln  Val  Phe  Lys  Gln  Asp
                   20                      25                      30

Trp  Glu  His  Leu  Ala  Tyr  Ser  Leu  Met  Phe  Val  Gly  Val  Asp  Gln  Leu
              35                      40                      45

Lys  Lys  Phe  Ser  Val  Asp  Glu  Val  Arg  His  Ala  Val  Glu  Arg  Leu  Asp
         50                     55                      60

Val  Arg  Gln  His  Val  Gly  Thr  Gln  Tyr  Tyr  Glu  Arg  Tyr  Ile  Ile  Ala
    65                      70                      75                      80

Thr  Ala  Thr  Leu  Leu  Val  Glu  Thr  Gly  Val  Ile  Thr  Gln  Ala  Glu  Leu
                        85                      90                      95

Asp  Gln  Ala  Leu  Gly  Ser  His  Phe  Lys  Leu  Ala  Asn  Pro  Ala  His  Ala
                   100                     105                     110

Thr  Gly  Arg  Pro  Ala  Ile  Thr  Gly  Arg  Pro  Pro  Phe  Glu  Val  Gly  Asp
              115                     120                     125

Arg  Val  Val  Val  Arg  Asp  Glu  Tyr  Val  Ala  Gly  His  Ile  Arg  Met  Pro
         130                     135                     140

Ala  Tyr  Val  Arg  Gly  Lys  Glu  Gly  Val  Val  Leu  His  Arg  Thr  Ser  Glu
    145                     150                     155                      160

Gln  Trp  Pro  Phe  Pro  Asp  Ala  Ile  Gly  His  Gly  Asp  Leu  Ser  Ala  Ala
                        165                     170                     175

His  Gln  Pro  Thr  Tyr  His  Val  Glu  Phe  Arg  Val  Lys  Asp  Leu  Trp  Gly
                   180                     185                     190

Asp  Ala  Ala  Asp  Asp  Gly  Tyr  Val  Val  Val  Asp  Leu  Phe  Glu  Ser  Tyr
              195                     200                     205

Leu  Asp  Lys  Ala  Pro  Gly  Ala  Gln  Ala  Val  Asn  Ala
         210                     215                     220
```

( 2 ) INFORMATION FOR SEQ ID NO:3:

( i ) SEQUENCE CHARACTERISTICS:
        ( A ) LENGTH: 600 base pairs
        ( B ) TYPE: nucleic acid ( C ) STRANDEDNESS: single
( D ) TOPOLOGY: linear ( i i ) MOLECULE TYPE: DNA (genomic)

( v i ) ORIGINAL SOURCE:
   ( A ) ORGANISM: Pseudomonas chlororaphis
   ( B ) STRAIN: B23 (FERM BP-187)

( x i ) SEQUENCE DESCRIPTION: SEQ ID NO:3:

| | | | | | | |
|---|---|---|---|---|---|---|
| ATGAGTACAT | CTATTTCCAC | GACTGCGACA | CCTTCGACAC | CCGGCGAGAG | GGCATGGGCC | 60 |
| TTGTTTCAAG | TGCTCAAGAG | CAAGGAACTC | ATCCAGAGG | GCTATGTCGA | GCAGCTCACT | 120 |
| CAATTGATGG | CCCATGACTG | GAGCCCGGAG | AACGGCGCTC | GCGTGGTCGC | CAAGGCATGG | 180 |
| GTCGATCCGC | AGTTCCGGGC | GCTGCTGCTC | AAGGACGGAA | CAGCCGCTTG | CGCGCAGTTC | 240 |
| GGCTACACCG | GCCCACAAGG | CGAATACATC | GTCGCCCTGG | AAGATACACC | GGGGGTGAAG | 300 |
| AACGTCATCG | TCTGCAGCCT | GTGCTCCTGC | ACCAACTGGC | CGGTCCTCGG | CCTGCCGCCC | 360 |
| GAGTGGTACA | AGGGCTTTGA | GTTTCGTGCG | CGCCTGGTCC | GGGAGGGGCG | CACCGTACTG | 420 |
| CGCGAGCTGG | GGACGGAGTT | GCCGAGCGAC | ACGGTCATCA | AAGTCTGGGA | TACCAGCGCC | 480 |
| GAAAGCCGTT | ACCTGGTGTT | GCCGCAAAGG | CCTGAAGGCT | CTGAGCACAT | GAGTGAAGAA | 540 |
| CAGCTTCAAC | AGCTGGTGAC | CAAAGACGTG | CTGATTGGCG | TCGCCCTGCC | ACGCGTTGGC | 600 |

( 2 ) INFORMATION FOR SEQ ID NO:4:

( i ) SEQUENCE CHARACTERISTICS:
      ( A ) LENGTH: 660 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Pseudomonas chlororaphis
      ( B ) STRAIN: B23 (FERM BP-187)

( x i ) SEQUENCE DESCRIPTION: SEQ ID NO:4:

| | | | | | | |
|---|---|---|---|---|---|---|
| ATGGATGGCT | TTCACGATCT | CGGCGGTTTC | CAAGGCTTTG | GCAAAGTGCC | GCACACCATC | 60 |
| AACAGCCTCA | GCTACAAACA | GGTTTTCAAG | CAGGACTGGG | AACACCTGGC | CTATAGCTTG | 120 |
| ATGTTTGTCG | GCGTTGACCA | ATTGAAAAAG | TTCAGCGTGG | ACGAAGTGCG | TCATGCCGTC | 180 |
| GAACGCCTGG | ACGTTCGCCA | GCATGTCGGC | ACCCAGTACT | ACGAACGCTA | CATCATCGCG | 240 |
| ACCGCCACGC | TGCTGGTGGA | AACGGGCGTT | ATCACCCAGG | CGGAGCTCGA | TCAGGCATTG | 300 |
| GGTTCCCACT | TCAAGCTGGC | GAACCCCGCC | CATGCGACAG | GTCGCCCGGC | GATCACCGGC | 360 |
| AGGCCGCCCT | TCGAAGTGGG | CGATCGGGTT | GTGGTTCGAG | ACGAATATGT | GGCGGGGCAT | 420 |
| ATCCGCATGC | CGGCCTACGT | GCGCGGTAAG | GAAGGCGTGG | TCCTGCACCG | CACCTCAGAG | 480 |
| CAGTGGCCCT | TCCCCGACGC | CATTGGCCAC | GGCGACTTGA | GCGCAGCCCA | TCAGCCTACC | 540 |
| TACCACGTCG | AGTTTCGCGT | GAAAGATCTA | TGGGGTGACG | CGGCAGATGA | CGGTTACGTC | 600 |
| GTGGTCGATC | TTTTCGAAAG | CTACTTGGAT | AAGGCCCCCG | GTGCCCAAGC | GGTGAACGCA | 660 |

( 2 ) INFORMATION FOR SEQ ID NO:5:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
  ( A ) ORGANISM: Pseudomonas chlororaphis
  ( B ) STRAIN: B23 (FERM BP-187)

( x i ) SEQUENCE DESCRIPTION: SEQ ID NO:5:

Ser Thr Ser Ile Ser Thr Thr Ala Thr Pro Ser Thr Pro Gly Glu Arg
1               5                   10                  15

Ala Trp Ala Leu Phe Gln Val Leu Lys
            20              25

( 2 ) INFORMATION FOR SEQ ID NO:6:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: Pseudomonas chlororaphis
    ( B ) STRAIN: B23 (FERM BP-187)

( x i ) SEQUENCE DESCRIPTION: SEQ ID NO:6:

Met Asp Gly Phe His Asp Leu Gly Gly Phe Gln Gly Phe Gly Lys Val
1               5                   10                  15

Pro His Thr Ile Asn Ser Leu
            20

( 2 ) INFORMATION FOR SEQ ID NO:7:

( i ) SEQUENCE CHARACTERISTICS:
    ( A ) LENGTH: 2070 base pairs
    ( B ) TYPE: nucleic acid
    ( C ) STRANDEDNESS: single
    ( D ) TOPOLOGY: linear ( i i ) MOLECULE TYPE: DNA (genomic)

( v i ) ORIGINAL SOURCE:
    ( A ) ORGANISM: Rhodococcus
    ( B ) STRAIN: sp. N-774 (FERM BP- 1936)

( i x ) FEATURE:
    ( A ) NAME/KEY: CDS
    ( B ) LOCATION: 675..1295

( i x ) FEATURE:
    ( A ) NAME/KEY: CDS
    ( B ) LOCATION: 1325..1960

( x i ) SEQUENCE DESCRIPTION: SEQ ID NO:7:

```
GCATGCTTTC CACATCTGGA ACGTGATCGC CACGGACGGT GGTGCCTACC AGATGTTGGA      60
CGGCAACGGA TACGGCATGA ACGCCGAAGG TTTGTACGAT CCGGAACTGA TGCACACTT      120
TGCTTCTCGA CGCATTCAGC ACGCCGACGC TCTGTCCGAA ACCGTCAAAC TGGTGGCCCT     180
GACCGGCCAC CACGGCATCA CCACCCTCGG CGGCGCGAGC TACGGCAAAG CCCGGAACCT     240
CGTACCGCTT GCCCGCGCCG CCTACGACAC TGCCTTGAGA CAATTCGACG TCCTGGTGAT     300
GCCAACGCTG CCCTACGTCG CATCCGAATT GCCGGCGAAG GACGTAGATC GTGCAACCTT     360
CATCACCAAG GCTCTCGGGA TGATCGCCAA CACGGCACCA TTCGACGTGA CCGGACATCC     420
GTCCCTGTCC GTTCCGGCCG GCCTGGTGAA CGGGGTTCCG GTCGGAATGA TGATCACCGG     480
CAGACACTTC GACGATGCGA CAGTCCTTCG TGTCGGACGC GCATTCGAAA AGCTTCGCGG     540
CCGGTTTCCG ACGCCGGCCG AACGCGCCTC CAACTCTGCA CCACAACTCA GCCCCGCCTA     600
```

```
GTCCTGACGC ACTGTCAGAC AACAAATTCC ACCGATTCAC ACATGATCAG CCCACATAAG              660

AAAAGGTGAA CCAG ATG TCA GTA ACG ATC GAC CAC ACA ACG GAG AAC GCC                710
              Met Ser Val Thr Ile Asp His Thr Thr Glu Asn Ala
              1           5                       10

GCA CCG GCC CAG GCG GCG GTC TCC GAC CGG GCG TGG GCA CTG TTC CGC                758
Ala Pro Ala Gln Ala Ala Val Ser Asp Arg Ala Trp Ala Leu Phe Arg
        15              20                      25

GCA CTC GAC GGT AAG GGA TTG GTA CCC GAC GGT TAC GTC GAG GGA TGG                806
Ala Leu Asp Gly Lys Gly Leu Val Pro Asp Gly Tyr Val Glu Gly Trp
    30              35                      40

AAG AAG ACC TCC GAG GAG GAC TTC AGT CCA AGG CGC GGA GCG GAA TTG                854
Lys Lys Thr Ser Glu Glu Asp Phe Ser Pro Arg Arg Gly Ala Glu Leu
45                  50                  55                  60

GTA GCG CGC GCA TGG ACC GAC CCC GAG TTC CGG CAG CTG CTT CTC ACC                902
Val Ala Arg Ala Trp Thr Asp Pro Glu Phe Arg Gln Leu Leu Leu Thr
            65                  70                  75

GAC GGT ACC GCC GCA GTT GCC CAG TAC GGA TAC CTG GGC CCC CAG GCG                950
Asp Gly Thr Ala Ala Val Ala Gln Tyr Gly Tyr Leu Gly Pro Gln Ala
        80                  85                      90

GCC TAC ATC GTG GCA GTC GAA GAC ACC CCG ACA CTC AAG AAC GTG ATC                998
Ala Tyr Ile Val Ala Val Glu Asp Thr Pro Thr Leu Lys Asn Val Ile
            95                  100                 105

GTG TGC TCG CTG TGT TCA TGC ACC GCG TGG CCC ATC CTC GGT CTG CCA                1046
Val Cys Ser Leu Cys Ser Cys Thr Ala Trp Pro Ile Leu Gly Leu Pro
    110                 115                 120

CCC ACC TGG TAC AAG AGC TTC GAA TAC CGT GCG CGC GTG GTC CGC GAA                1094
Pro Thr Trp Tyr Lys Ser Phe Glu Tyr Arg Ala Arg Val Val Arg Glu
125                 130                 135                 140

CCA CGG AAG GTT CTC TCC GAG ATG GGA ACC GAG ATC GCG TCG GAC ATC                1142
Pro Arg Lys Val Leu Ser Glu Met Gly Thr Glu Ile Ala Ser Asp Ile
                145                 150                 155

GAG ATT CGC GTC TAC GAC ACC ACC GCC GAA ACT CGC TAC ATG GTC CTC                1190
Glu Ile Arg Val Tyr Asp Thr Thr Ala Glu Thr Arg Tyr Met Val Leu
        160                 165                 170

CCG CAG CGT CCC GCC GGC ACC GAA GGC TGG AGC CAG GAA CAA CTG CAG                1238
Pro Gln Arg Pro Ala Gly Thr Glu Gly Trp Ser Gln Glu Gln Leu Gln
    175                 180                 185

GAA ATC GTC ACC AAG GAC TGC CTG ATC GGG GTT GCA ATC CCG CAG GTT                1286
Glu Ile Val Thr Lys Asp Cys Leu Ile Gly Val Ala Ile Pro Gln Val
190                 195                 200

CCC ACC GTC TGATCACCCC GACAAGAAGG AAGCACACC ATG GAT GGA GTA CAC                1339
Pro Thr Val                                     Met Asp Gly Val His
205                                             1               5

GAT CTT GCC GGA GTA CAA GGC TTC GGC AAA GTC CCG CAT ACC GTC AAC                1387
Asp Leu Ala Gly Val Gln Gly Phe Gly Lys Val Pro His Thr Val Asn
            10                  15                      20

GCC GAC ATC GGC CCC ACC TTT CAC GCC GAA TGG GAA CAC CTG CCC TAC                1435
Ala Asp Ile Gly Pro Thr Phe His Ala Glu Trp Glu His Leu Pro Tyr
        25                  30                      35

AGC CTG ATG TTC GCC GGT GTC GCC GAA CTC GGG GCC TTC AGC GTC GAC                1483
Ser Leu Met Phe Ala Gly Val Ala Glu Leu Gly Ala Phe Ser Val Asp
            40                  45                      50

GAA GTG CGA TAC GTC GTC GAG CGG ATG GAG CCG GGC CAC TAC ATG ATG                1531
Glu Val Arg Tyr Val Val Glu Arg Met Glu Pro Gly His Tyr Met Met
    55                  60                  65

ACC CCG TAC TAC GAG AGG TAC GTC ATC GGT GTC GCG ACA TTG ATG GTC                1579
Thr Pro Tyr Tyr Glu Arg Tyr Val Ile Gly Val Ala Thr Leu Met Val
70                  75                      80                  85

GAA AAG GGA ATC CTG ACG CAG GAC GAA CTC GAA AGC CTT GCG GGG GGA                1627
```

|     |     |     |     |     |     |     |     |     |     |     |     |     |     |      |
|-----|-----|-----|-----|-----|-----|-----|-----|-----|-----|-----|-----|-----|-----|------|
| Glu | Lys | Gly | Ile | Leu | Thr | Gln | Asp | Glu | Leu | Glu | Ser | Leu | Ala | Gly Gly |
|     |     |     |     | 90  |     |     |     |     | 95  |     |     |     |     | 100 |

| CCG | TTC | CCA | CTG | TCA | CGG | CCC | AGC | GAA | TCC | GAA | GGG | CGG | CCG | GCA | CCC | 1675 |
|-----|-----|-----|-----|-----|-----|-----|-----|-----|-----|-----|-----|-----|-----|-----|-----|------|
| Pro | Phe | Pro | Leu | Ser | Arg | Pro | Ser | Glu | Ser | Glu | Gly | Arg | Pro | Ala | Pro |      |
|     |     |     | 105 |     |     |     |     | 110 |     |     |     |     | 115 |     |     |      |

| GTC | GAG | ACG | ACC | ACC | TTC | GAA | GTC | GGG | CAG | CGA | GTA | CGC | GTA | CGC | GAC | 1723 |
| Val | Glu | Thr | Thr | Thr | Phe | Glu | Val | Gly | Gln | Arg | Val | Arg | Val | Arg | Asp |      |
|     |     | 120 |     |     |     |     | 125 |     |     |     |     | 130 |     |     |     |      |

| GAG | TAC | GTT | CCG | GGG | CAT | ATT | CGA | ATG | CCT | GCA | TAC | TGC | CGT | GGA | CGA | 1771 |
| Glu | Tyr | Val | Pro | Gly | His | Ile | Arg | Met | Pro | Ala | Tyr | Cys | Arg | Gly | Arg |      |
|     | 135 |     |     |     |     | 140 |     |     |     |     | 145 |     |     |     |     |      |

| GTG | GGA | ACC | ATC | TCT | CAT | CGA | ACT | ACC | GAG | AAG | TGG | CCG | TTT | CCC | GAC | 1819 |
| Val | Gly | Thr | Ile | Ser | His | Arg | Thr | Thr | Glu | Lys | Trp | Pro | Phe | Pro | Asp |      |
| 150 |     |     |     |     | 155 |     |     |     |     | 160 |     |     |     |     | 165 |      |

| GCA | ATC | GGC | CAC | GGG | CGC | AAC | GAC | GCC | GGC | GAA | GAA | CCG | ACG | TAC | CAC | 1867 |
| Ala | Ile | Gly | His | Gly | Arg | Asn | Asp | Ala | Gly | Glu | Glu | Pro | Thr | Tyr | His |      |
|     |     |     |     | 170 |     |     |     |     | 175 |     |     |     |     | 180 |     |      |

| GTG | AAG | TTC | GCC | GCC | GAG | GAA | TTG | TTC | GGT | AGC | GAC | ACC | GAC | GGT | GGA | 1915 |
| Val | Lys | Phe | Ala | Ala | Glu | Glu | Leu | Phe | Gly | Ser | Asp | Thr | Asp | Gly | Gly |      |
|     |     |     | 185 |     |     |     |     | 190 |     |     |     |     | 195 |     |     |      |

| AGC | GTC | GTT | GTC | GAC | CTC | TTC | GAG | GGT | TAC | CTC | GAG | CCT | GCG | GCC | | 1960 |
| Ser | Val | Val | Val | Asp | Leu | Phe | Glu | Gly | Tyr | Leu | Glu | Pro | Ala | Ala | |      |
|     | 200 |     |     |     |     | 205 |     |     |     |     | 210 |     |     |     | |      |

| TGATCTTCCA | GCATTCCAGG | CGGCGGTCAC | GCGATCACAG | CGGTTCGTGC | GACCGCCGCC | 2020 |
|------------|------------|------------|------------|------------|------------|------|
| TGATCACCAC | GATTCACTCA | TTCGGAAGGA | CACTGGAAAT | CATGGTCGAC |            | 2070 |

( 2 ) INFORMATION FOR SEQ ID NO:8:

( i ) SEQUENCE CHARACTERISTICS:
        ( A ) LENGTH: 2456 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Pseudomonas chlororaphis
        ( B ) STRAIN: B23 (FERM BP-187)

( i x ) FEATURE:
        ( A ) NAME/KEY: CDS
        ( B ) LOCATION: 1021..1620

( i x ) FEATURE:
        ( A ) NAME/KEY: CDS
        ( B ) LOCATION: 1666..2325

( x i ) SEQUENCE DESCRIPTION: SEQ ID NO:8:

| GGATCCCGTC | GGCCTTCTGC | GGTACCTACG | GCATGAAGCC | CACCCACGGC | CTGGTGCCCT | 60  |
|------------|------------|------------|------------|------------|------------|-----|
| ACACCGGCGT | CATGGCGATT | GAAGCCACGA | TCGATCATGT | CGGCCCCATC | ACCGGTAACG | 120 |
| TGCGCGACAA | CGCGCTGATG | CTGCAGGCAA | TGGCCGGTGC | AGACGGACTC | GACCCGCGCC | 180 |
| AGGCGGCGCC | TCAGGTCGAT | GACTATTGCA | GTTACCTGGA | AAAAGGCGTG | AGCGGACTCA | 240 |
| GAATCGGGGT | GTTGCAAGAG | GGATTCGCGC | TTGCTAACCA | GGACCCTCGC | GTGGCGGACA | 300 |
| AAGTCGCGGA | CGCCATCGCC | CGACTCGAGG | CGTTGGGCGC | TCATGTCGAG | CCGGTCTCCA | 360 |
| TTCCCGAGCA | CAACCTGGCA | GGGTTGTTGT | GGCACCCCAT | CGGTTGCGAA | GGCTTGACCA | 420 |
| TGCAGATGAT | GCATGGCAAC | GGCGCAGGCT | TAACTGGAA  | AGGACTTTAC | GATGTCGGCC | 480 |
| TGCTGGACAA | ACAAGCCAGC | TGGCGCGACG | ACGCAGACCA | ATTATCCGCG | TCGCTCAAGC | 540 |
| TCTGCATGTT | CGTCGGCCAA | TACGGCCTGT | CGCGCTACAA | CGGACGCTAC | TACGCCAAGG | 600 |

-continued

| | | | | | |
|---|---|---|---|---|---|
| CCCAGAACCT | TGCACGCTTT | GCCCGGCAGG | GATACGACAA | AGCGCTGCAA | ACCTATGACC | 660 |
| TGCTGGTGAT | GCCGACCACG | CCCATCACGG | CCCAACCCCA | CCCGCCAGCG | AACTGCTCGA | 720 |
| TCACGGAGTA | CGTGGCTCGC | GCGTTGGAAA | TGATCGGCAA | TACCGCGCCA | CAGGACATCA | 780 |
| CCGGGCATCC | GGCCATGTCG | ATTCCGTGTG | GCCTGCTGGA | CGGCCTGCCC | GTCGGGCTGA | 840 |
| TGCTGGTCGC | AAAACACTAC | GCCGAGGGCA | CGATTTACCA | AGCGGCGGCG | GCGTTTGAAG | 900 |
| CCTCGGTGGA | CTGGCGCACG | CTCTGAGCCT | TTTACAGGCG | CCGCCCCCC | TGAAGAACGA | 960 |
| TAAGAAAGAC | CGGCAAGTTG | CAATGACTTT | TCAACCGCGT | TGACTGATAG | GAGTTACCCC | 1020 |

```
ATG AGT ACA TCT ATT TCC ACG ACT GCG ACA CCT TCG ACA CCC GGC GAG        1068
Met Ser Thr Ser Ile Ser Thr Thr Ala Thr Pro Ser Thr Pro Gly Glu
 1           5                  10                 15

AGG GCA TGG GCC TTG TTT CAA GTG CTC AAG AGC AAG GAA CTC ATC CCA        1116
Arg Ala Trp Ala Leu Phe Gln Val Leu Lys Ser Lys Glu Leu Ile Pro
             20                 25                 30

GAG GGC TAT GTC GAG CAG CTC ACT CAA TTG ATG GCC CAT GAC TGG AGC        1164
Glu Gly Tyr Val Glu Gln Leu Thr Gln Leu Met Ala His Asp Trp Ser
         35                 40                 45

CCG GAG AAC GGC GCT CGC GTG GTC GCC AAG GCA TGG GTC GAT CCG CAG        1212
Pro Glu Asn Gly Ala Arg Val Val Ala Lys Ala Trp Val Asp Pro Gln
 50                 55                 60

TTC CGG GCG CTG CTG CTC AAG GAC GGA ACA GCC GCT TGC GCG CAG TTC        1260
Phe Arg Ala Leu Leu Leu Lys Asp Gly Thr Ala Ala Cys Ala Gln Phe
 65                 70                 75                 80

GGC TAC ACC GGC CCA CAA GGC GAA TAC ATC GTC GCC CTG GAA GAT ACA        1308
Gly Tyr Thr Gly Pro Gln Gly Glu Tyr Ile Val Ala Leu Glu Asp Thr
             85                 90                 95

CCG GGG GTG AAG AAC GTC ATC GTC TGC AGC CTG TGC TCC TGC ACC AAC        1356
Pro Gly Val Lys Asn Val Ile Val Cys Ser Leu Cys Ser Cys Thr Asn
             100                105                110

TGG CCG GTC CTC GGC CTG CCG CCC GAG TGG TAC AAG GGC TTT GAG TTT        1404
Trp Pro Val Leu Gly Leu Pro Pro Glu Trp Tyr Lys Gly Phe Glu Phe
             115                120                125

CGT GCG CGC CTG GTC CGG GAG GGG CGC ACC GTA CTG CGC GAG CTG GGG        1452
Arg Ala Arg Leu Val Arg Glu Gly Arg Thr Val Leu Arg Glu Leu Gly
 130                135                140

ACG GAG TTG CCG AGC GAC ACG GTC ATC AAA GTC TGG GAT ACC AGC GCC        1500
Thr Glu Leu Pro Ser Asp Thr Val Ile Lys Val Trp Asp Thr Ser Ala
145                 150                155                160

GAA AGC CGT TAC CTG GTG TTG CCG CAA AGG CCT GAA GGC TCT GAG CAC        1548
Glu Ser Arg Tyr Leu Val Leu Pro Gln Arg Pro Glu Gly Ser Glu His
             165                170                175

ATG AGT GAA GAA CAG CTT CAA CAG CTG GTG ACC AAA GAC GTG CTG ATT        1596
Met Ser Glu Glu Gln Leu Gln Gln Leu Val Thr Lys Asp Val Leu Ile
             180                185                190

GGC GTC GCC CTG CCA CGC GTT GGC TGAGAAAAAA CAACTCATCA TCGTTCAACT       1650
Gly Val Ala Leu Pro Arg Val Gly
             195                200

TGCGGAGTTT TCATT ATG GAT GGC TTT CAC GAT CTC GGC GGT TTC CAA GGC       1701
              Met Asp Gly Phe His Asp Leu Gly Gly Phe Gln Gly
               1           5                  10

TTT GGC AAA GTG CCG CAC ACC ATC AAC AGC CTC AGC TAC AAA CAG GTT        1749
Phe Gly Lys Val Pro His Thr Ile Asn Ser Leu Ser Tyr Lys Gln Val
         15                 20                 25

TTC AAG CAG GAC TGG GAA CAC CTG GCC TAT AGC TTG ATG TTT GTC GGC        1797
Phe Lys Gln Asp Trp Glu His Leu Ala Tyr Ser Leu Met Phe Val Gly
         30                 35                 40

GTT GAC CAA TTG AAA AAG TTC AGC GTG GAC GAA GTG CGT CAT GCC GTC        1845
Val Asp Gln Leu Lys Lys Phe Ser Val Asp Glu Val Arg His Ala Val
```

-continued

| | | | | 45 | | | | | 50 | | | | | 55 | | | | | 60 | |
|---|---|---|---|---|---|---|---|---|---|---|---|---|---|---|---|---|---|---|---|---|
| GAA | CGC | CTG | GAC | GTT | CGC | CAG | CAT | GTC | GGC | ACC | CAG | TAC | TAC | GAA | CGC | | | | | 1893 |
| Glu | Arg | Leu | Asp | Val | Arg | Gln | His | Val | Gly | Thr | Gln | Tyr | Tyr | Glu | Arg | | | | | |
| | | | | 65 | | | | | 70 | | | | | 75 | | | | | | |
| TAC | ATC | ATC | GCG | ACC | GCC | ACG | CTG | CTG | GTG | GAA | ACG | GGC | GTT | ATC | ACC | | | | | 1941 |
| Tyr | Ile | Ile | Ala | Thr | Ala | Thr | Leu | Leu | Val | Glu | Thr | Gly | Val | Ile | Thr | | | | | |
| | | | 80 | | | | | 85 | | | | | 90 | | | | | | | |
| CAG | GCG | GAG | CTC | GAT | CAG | GCA | TTG | GGT | TCC | CAC | TTC | AAG | CTG | GCG | AAC | | | | | 1989 |
| Gln | Ala | Glu | Leu | Asp | Gln | Ala | Leu | Gly | Ser | His | Phe | Lys | Leu | Ala | Asn | | | | | |
| | | 95 | | | | | 100 | | | | | 105 | | | | | | | | |
| CCC | GCC | CAT | GCG | ACA | GGT | CGC | CCG | GCG | ATC | ACC | GGC | AGG | CCG | CCC | TTC | | | | | 2037 |
| Pro | Ala | His | Ala | Thr | Gly | Arg | Pro | Ala | Ile | Thr | Gly | Arg | Pro | Pro | Phe | | | | | |
| | 110 | | | | | 115 | | | | | 120 | | | | | | | | | |
| GAA | GTG | GGC | GAT | CGG | GTT | GTG | GTT | CGA | GAC | GAA | TAT | GTG | GCG | GGG | CAT | | | | | 2085 |
| Glu | Val | Gly | Asp | Arg | Val | Val | Val | Arg | Asp | Glu | Tyr | Val | Ala | Gly | His | | | | | |
| 125 | | | | | 130 | | | | | 135 | | | | | 140 | | | | | |
| ATC | CGC | ATG | CCG | GCC | TAC | GTG | CGC | GGT | AAG | GAA | GGC | GTG | GTC | CTG | CAC | | | | | 2133 |
| Ile | Arg | Met | Pro | Ala | Tyr | Val | Arg | Gly | Lys | Glu | Gly | Val | Val | Leu | His | | | | | |
| | | | | 145 | | | | | 150 | | | | | 155 | | | | | | |
| CGC | ACC | TCA | GAG | CAG | TGG | CCC | TTC | CCC | GAC | GCC | ATT | GGC | CAC | GGC | GAC | | | | | 2181 |
| Arg | Thr | Ser | Glu | Gln | Trp | Pro | Phe | Pro | Asp | Ala | Ile | Gly | His | Gly | Asp | | | | | |
| | | | 160 | | | | | 165 | | | | | 170 | | | | | | | |
| TTG | AGC | GCA | GCC | CAT | CAG | CCT | ACC | TAC | CAC | GTC | GAG | TTT | CGC | GTG | AAA | | | | | 2229 |
| Leu | Ser | Ala | Ala | His | Gln | Pro | Thr | Tyr | His | Val | Glu | Phe | Arg | Val | Lys | | | | | |
| | | 175 | | | | | 180 | | | | | 185 | | | | | | | | |
| GAT | CTA | TGG | GGT | GAC | GCG | GCA | GAT | GAC | GGT | TAC | GTC | GTG | GTC | GAT | CTT | | | | | 2277 |
| Asp | Leu | Trp | Gly | Asp | Ala | Ala | Asp | Asp | Gly | Tyr | Val | Val | Val | Asp | Leu | | | | | |
| | 190 | | | | | 195 | | | | | 200 | | | | | | | | | |
| TTC | GAA | AGC | TAC | TTG | GAT | AAG | GCC | CCC | GGT | GCC | CAA | GCG | GTG | AAC | GCA | | | | | 2325 |
| Phe | Glu | Ser | Tyr | Leu | Asp | Lys | Ala | Pro | Gly | Ala | Gln | Ala | Val | Asn | Ala | | | | | |
| 205 | | | | | 210 | | | | | 215 | | | | | 220 | | | | | |

| TGATTGAAGG | CGCCCAGGCG | GGCCGACTGC | CGGTGACGGT | CCTTTCCGGC | TTCCTCGGCG | 2385 |
| CCGGCAAAAC | CACCCTGCTC | AACGCTATCC | TGCGAAATCG | CCAAGGACTG | CGGGTCGCGG | 2445 |
| TCATCGTCAA | C | | | | | 2456 |

GENE ENCODING A POLYPEPTIDE HAVING NITRILE HYDRATASE ACTIVITY, A TRANSFORMANT CONTAINING THE GENE AND A PROCESS FOR THE PRODUCTION OF AMIDES USING THE TRANSFORMANT

This is a continuation of application Ser. No. 08/233,146, filed Apr. 22, 1994; U.S. Pat. No. 5,648,256 which in turn is a continuation of application Ser. No. 07/694,746 filed on May 2, 1991 now abandoned.

FIELD OF THE INVENTION

The present invention relates to a gene which is derived from *Pseudomonas chlororaphis* B23 and which encodes a polypeptide having nitrile hydratase activity to hydrate nitrites to amides. The invention also relates to a recombinant DNA containing the gene, and a transformant transformed with the recombinant DNA. The present invention further relates to a method of the production of nitrile hydratase using the transformant and of amides using nitrile hydratase.

PRIOR ART

Nitrile hydratase or nitrilase is known as an enzyme that hydrates nitriles to amides. Microorganisms that produce nitrile hydratase include those belonging to the genus Bacillus, the genus Bacteridium, the genus Micrococcus and the genus Brevibacterium (See, JP-B-62-21517/1989, U.S. Pat. No. No. 4,001,081), the genus Corynebacterium and the genus Nocardia (See, JP-B-56-17918/1989, U.S. Pat. No. 4,248,968), the genus Pseudomonas (See, JP-B-59-37951/1984, U.S. Pat. No. 4,637,982), the genus Rhodococcus, the genus Arthrobacter and the genus Microbacterium (See, JP-A-61-162193/1986, EP-A-0188316), and *Rhodococcus rhodochrous* (See, JP-A-2-470/1990, EP-A-0307926).

Nitrile hydratase has been used to hydrate nitriles to amides. In the invention, microorganisms are engineered to contain multiple copies of a recombinant DNA encoding nitrile hydratase according to a recombinant DNA technology. The recombinant produces a remarkably high level of nitrile hydratase compared with conventional methods.

The present inventors previously disclosed a gene derived from *Rhodococcus sp.* N-774 (FERM BP-1936) which also encodes a polypeptide having nitrile hydratase activity (JP-A-2-119778/1988).

In contrast, the present inventors utilized a gene derived from *Pseudomonas chlororaphis* B23-described in said U.S. Pat. No. 4,637,982 for the production of nitrile hydratase. We isolated the gene encoding nitrile hydratase, inserted the gene into a suitable plasmid vector and transformed an appropriate host with the recombinant plasmid, thus successfully obtained the transformant producing nitrile hydratase.

SUMMARY OF THE INVENTION

The present invention relates to:

(1) a gene encoding a polypeptide which has nitrile hydratase activity and which comprises α-subunit of the following amino acid sequence as defined in the Sequence Listing by SEQ ID: No. 1, and β-subunit of the following amino acid sequence as defined in the Sequence Listing by SEQ ID: No. 2.

(2) a gene as described in (1) encoding α- and β-subunits, comprising α-subunit-encoding sequence as defined in the Sequence Listing by SEQ ID: No. 3, and β-subunit-encoding sequence as defined in the Sequence Listing by SEQ ID: No. 4.

(3) a recombinant DNA comprising a vector containing the gene as described in (1) or (2);

(4) a transformant transformed with the recombinant DNA as described in (3);

(5) a method for the production of nitrile hydratase which comprises culturing the transformant as described in (4) and recovering nitrile hydratase from the culture;

(6) a method for the production of amides which comprises hydrating nitriles using nitrile hydratase as described in (6) to form amides; and (7) a method for the production of amides which comprises culturing the transformant as described in (4), and hydrating nitriles using the resultant culture isolated bacterial cells, treated matter thereof, or a fixed material of them, to form amides.

The present invention is described in detail as follows:

(1) Isolation and Purification of Nitrile Hydratase and Partial Amino Acid Sequencing of Nitrile Hydratase Nitrile hydratase is isolated and purified from *Pseudomonas chlororaphis* B23 and separated into α and β subunits using HPLC. N-Terminal amino acid sequence of the subunits is determined and shown in the Sequence Listing by SEQ ID: No. 5 and No. 6, respectively.

(2) Preparation of a DNA Probe for a Nitrile Hydratase Gene

A DNA probe is prepared from JM105/pYUK121 (FERM BP-1937) as described in JP-A-2-119778/1990 due to the high degree of homology in the amino acid sequence between the nitrile hydratase β subunit of *Rhodococcus sp.* N-774 described in said Japanese Patent official gazette and that of *Pseudomonas chlororaphis* B23. Plasmid pYUK121 containing nitrile hydratase gene derived from *Rhodococcus sp.* N-774 is prepared from a JM10.5/pYUK121 culture. pYUK121 DNA is digested with SphI and SalI. The SphI-SalI fragment contains the nitrile hydratase gene (shown in the Sequence Listing as defined by SEQ ID: No. 7) of Rhodococcus sp. N-774. The DNA fragment is radiolabeled to give a probe.

(3) Detection of a DNA Segment Containing a Nitrile Hydratase Gene from the Chromosome of *Pseudomonas chlororaphis* B23

Chromosomal DNA is prepared from a *Pseudomonas chlororaphis* B23 culture. Chromosomal DNA is digested with restriction enzymes and hybridized to the probe described in (2), according to a Southern hybridization method [Southern, E. M., J. Mol. Biol. 98, 503 (1975)]. Two DNA fragments of different length are screened.

(4) Construction of a Recombinant Plasmid

A recombinant plasmid is constructed by inserting the chromosomal DNA fragment as prepared in (3) into a plasmid vector.

(5) Transformation and Screening of the Transformant Containing the Recombinant Plasmid Transformants are prepared using the recombinant plasmid as described in (4). The transformant containing the recombinant plasmid is selected using the probe as described in (2) according to a colony hybridization method [R. Bruce Wallace et. al., Nuc. Aci. Res. 9,879 (1981)]. Additionally, the presence of the nitrile hydratase gene in the recombinant plasmid is confirmed using a Southern hybridization method. The plasmids thus selected are designated as pPCN1 and pPCN3.

(6) Isolation and Purification of Plasmid DNA and Construction of the Restriction Map Plasmid DNAs of pPCN1 and pPCN3 as described in (5) are isolated and purified. The restriction maps of the DNAs are constructed (FIG. 1) to determine the region containing nitrile hydratase gene.

(7) DNA Sequencing

The extra segment of the inserted DNA fragment in pPCN1 and pPCN3 is excised using an appropriate restriction enzyme. The inserted DNA fragment is then used for sequencing. The nucleotide sequence of the DNA fragment. (see, the Sequence Listing as defined by SEQ ID: No. 8) reveals that it contains the sequence deduced from the amino acid sequence as described in (1).

(8) Insertion of the DNA Fragment into an Expression Vector and Transformation

The DNA fragment is cleaved from pPCN1 and pPCN3 using appropriate-restriction enzymes. These two fragments are ligated and inserted into an expression vector pUC19. The construct is used for transformation of *E. coli* JM105 (Amersham), and the transformant is designated as JM105/pPCN4.

(9) Production of Nitrile Hydratase Using the Transformant and Conversion of Nitriles to Amides The transformant as described in (8) is cultured. The bacterial cells are mixed with nitriles, a substrate of nitrile hydratase, and amides are produced.

*Pseudomonas chlororaphis* B23 was deposited with Fermentation Research Institute, Agency of Industrial Science and Technology and was assigned the accession number FERM BP-187. A transformant JM105/pPCN4 was deposited with the same and assigned the accession number FERM BP-2779.

Any vector including a plasmid vector (e.g., pAT153, pMP9, pHC624, pKC7, etc.), a phage vector (e.g., λgt11 (Toyobo), Charon 4A (Amersham), etc. may be used for the present invention. Enzymes which may be used include, SphI, SalI, SacI, BamHI, EcoRI, PstI and the like, which are commercially available (Takara Shuzo). Various hosts may be used for transformation including but not limited to *E. coli* JM105 and TG1. Culture media for the transformant are those ordinarily used in the art.

Conversion of nitrites to amides is carried out using nitrile hydratase, crude nitrile hydratase, the culture of the transformant, the isolated bacterial cells or treated matter thereof, and the like, prepared from the culture of the transformant.

Suitable nitriles include those having 2-4 carbon atoms such as acetonitrile, propionitrile, acrylonitrile, methacrylonitrile, n-butyronitrile and isobutyronitrile, and acrylonitrile is preferred.

THE EFFECT OF THE INVENTION

The present invention have disclosed the amino acid sequence and nucleotide sequence of the α- and β-subunits of nitrile hydratase derived from *Pseudomonas chlororaphis* B23. The gene encoding nitrile hydratase is inserted into an expression vector and the recombinant vector is used for transformation. The transformant contains multiple copies of the gene and produces a higher level of nitrile hydratase compared with conventionally used microorganisms.

The present invention will be described in detail in the following Example which is never construed to limit the invention.

The following abbreviation is used in Example:
TE: Tris-HCl (10 mM; pH 7.8), EDTA (1 mM, pH 8.0)
TNE: Tris-HCl (50 mM; pH 8.0), EDTA (1 mM, pH 8.0), NaCl (50 mM)
STE: Tris-HCl (50 mM; pH 8.0), EDTA (5 mM, pH 8.0), Sucrose (35 mM)
2×YT medium: 1.6% Trypton; 1.0% Yeast extract, 0.5% NaCl

EXAMPLE (1) Isolation and Purification of Nitrile Hydratase and the Amino Acid Sequencing of a Portion of Nitrile Hydratase

*Pseudomonas chlororaphis* B23 was cultured in a medium (10 g/l of sucrose, 4 g/l of methacrylamide, 0.5 g/l of $KH_2PO_4$, 0.5 g/l of $K_2HPO_4$, 0.5 g/l of $MgSO_4.7H_2O$, 0.01 g/l of $FeSO_4.7H_2O$, pH 7.0) at 25° C. for 28 hours. The bacterial cells were harvested. 100 g of the bacterial cells was disrupted and fractionated with ammonium sulfate. The sample was dialyzed and the dialysate was centrifuged. The supernatant was removed and loaded on DEAE-Sephacel chromatography, Octyl-Sepharose CL-4B chromatography, Phenyl-Sepharose CL-4B chromatography and Sephadex G-150 chromatography. Active fractions were collected and dialyzed. The dialysate containing the enzyme was loaded on a high performance liquid chromatography using a reversed phase column (Senshu Pak VP-304-1251, Senshu Kagaku), and two subunits (α and β) were obtained. The N-terminal amino acid sequence of α- and β-subunits was determined using an amino acid sequencer (Applied Biosystems model 470A). N-terminal amino acid sequences of α- and β-subunits are shown in the Sequence Listing as defined by SEQ ID: No. 5 and. SEQ ID: No. 6 respectively.

(2) Preparation of a DNA Probe for Nitrile Hydratase Gene

*E. coli* JM105 containing pYUK121 (FERM BP-1937) was cultured in 100 ml of 2×YT medium containing 50 μg/ml of ampicillin at 30° C. overnight (12 hours). The bacterial cells were harvested and TNE was added to the cells. The cell suspension was then centrifuged. 8 ml of STE and 10 mg of lysozyme were added to the pellet. The mixture was incubated at 0° C. for five minutes followed by the addition of 4 ml of 0.25M EDTA. 2 ml of 10% SDS and 5 ml of 5M NaCl were then added to the mixture at room temperature. The resultant mixture was left standing at 0°–4° C. for three hours and then ultracentrifuged. ½ volume of 30% PEG 6000 was added to the supernatant. The mixture was allowed to stand at 0°–4° C. overnight (12 hours) and centrifuged. TNE was added to the pellet to bring the volume to 7.5 ml and CsCl was then added to the suspension. The mixture was centrifuged to remove proteins. Then, 300–500 mg/ml of ethidium bromide was added to the supernatant. The mixture was transferred to a centrifuge tube. The tube was heat-sealed and then ultracentrifuged. cccDNA was extracted using a peristaltic pump. A bit more than equal volume of isopropyl alcohol saturated with water was added to the extract to remove ethidium bromide. The sample was dialyzed against TE. About 3 ml of purified pYUK121 was obtained.

pYUK121 DNA was digested with SphI and SalI, resulting in a 2.07 kb DNA fragment containing a nitrile hydratase gene derived from Rhodococcus sp. N-774. The fragment was radiolabeled with $^{32}p$ to produce a probe. The nucleotide sequence of the probe is shown in the Sequence Listing as defined by SEQ ID: No. 7.

(3) Preparation of a DNA Fragment Containing a Nitrile Hydratase Gene of Chromosome

*Pseudomonas chlororaphis* B23 was cultured in 100 ml of the medium as described in (1). The bacterial cells were harvested and washed with TNE. The pellet was then suspended in 10 ml of TE. 4 ml of 0.25M EDTA, 10–20 mg of lysozyme. 10–20 mg of achromoprotease and 10 ml of 10% SDS were added to the suspension. The mixture was incubated at 37° C. for three hours. 15 ml of phenol was added to the mixture. The mixture was incubated at room temperature for 15 minutes and then centrifuged. To 15 ml of the upper layer, 0.7 ml of 2.5M sodium acetate and diethyl ether were added and the mixture was centrifuged. The upper layer was discarded. Two volumes of ethanol were added to the bottom layer and DNA was removed with a glass rod. DNA was rinsed with TE:ethanol 2:8, 1:9, and 0:10 (v/v) for five minutes each. DNA was then resuspended in 2–4 ml of TE (37° C.) 10 µl of a mixture of RNase A and $T_1$ was added to the suspension and the mixture was incubated at 30° C. An equal volume of phenol was added to the mixture. The mixture was then centrifuged. After centrifugation, 2–4 ml of the upper layer was removed. More than equal amount of ether was added to the removed portion. The mixture was centrifuged. After centrifugation, the upper layer was discarded. The bottom layer was dialyzed overnight against 2 l of TE containing a small amount of chloroform and further dialyzed against fresh TE for 3–4 hours. 4 ml of crude chromosomal DNA was obtained. Enzymatic digestion of chromosomal DNA was carried out as follows:

(a) 2 µl of SacI+3 µl of reaction buffer (10×)+15 µl of chromosomal DNA+10 µl of TE (b) 2 µl of BamHI+2 µl of SalI+3 µl of reaction buffer (10×)+15 µl of chromosomal DNA+8 µl of TE The mixtures were incubated at 37° C. for an hour and electrophoresed on an agarose gel at 60 V for three hours. The Southern hybridization of chromosomal DNA was carried out using the probe as described in (2). About 4.6 kb and 4.7 kb fragments were found to show a strong hybridization.

15 µl of chromosomal DNA was digested with SacI, and BamHI and SalI and electrophoresed on an agarose gel as described above. 4.6 kb and 4.7 kb DNA fragments were cut out from the gel and placed in three volumes of 8M $NaClO_4$. The solution was dotted on a GF/C (Whatman) filter paper (6 mm in diameter). Ten drops (≈100 µl) of TE containing 6M $NaClO_4$ and then ten drops (≈100 µl) of 95% ethanol were added to the filter paper. The paper was air-dried and placed in 0.5 ml Eppendorf tube. 40 µl of TE was added to the tube and the tube was incubated at 37° C. for 30 minutes. The tube was then centrifuged. About 40 µl of the supernatant was obtained which contained 4.6 kb and 4.7 kb DNA fragments containing a nitrile hydratase gene of chromosomal DNA.

(4) Insertion of the Chromosomal DNA Fragment into a Vector (a) 4.6 kb DNA Fragment 2 µl of SacI, 3 µl of reaction buffer (10×) and 10 µl of TE were added to 10 µl of pUC18 DNA. The mixture was incubated at 37° C. for an hour. 2 µl of 0.25 M EDTA was added to the mixture to stop the reaction. Then 7 µl of 1M Tris-HCl (pH 9) and 3 µl of BAP (bacterial alkaline phosphatase) were added to the mixture. The mixture was incubated at 65° C. for an hour. TE was then added to the mixture to bring the volume to 100 µl. The mixture was extracted 3× with an equal volume of phenol. An equal volume of ether was added to the extract. The bottom layer was removed and 10 µl of 3M sodium acetate and 250 µl of ethanol were added to the bottom layer. The mixture was incubated at –80° C. for 30 minutes, centrifuged, dried, and resuspended in TE.

5 µl of pUC18 DNA thus obtained and 40 µl of the 4.6 kb DNA fragment as described in (3) were mixed. 6 µl of ligation buffer, 6 µl of ATP (6 mg/ml) and 3 µl of T4 DNA ligase were added to the mixture. The mixture was incubated at 4° C. overnight (12 hours) to produce the recombinant plasmid containing the 4.6 kb DNA fragment in the SacI site of pUC18.

(b) 4.7 kb DNA Fragment pUC18 DNA was digested with BamHI and SalI. The 4.7 kb DNA fragment was inserted into the BamHI-SalI site of pUC18 in a similar manner as described in (4)-(a). The recombinant plasmid containing the 4.7 kb DNA fragment in the BamHI-SalI site of pUC18 was obtained.

(5) Transformation and Screening of Transformants

*E. coli* JM105 (Amersham) was inoculated into 10 ml of 2×YT medium and incubated at 37° C. for 12 hours. After incubation, the culture was added to a fresh 2×YT medium to a final concentration of 1%, and the mixture was incubated at 37° C. for two hours. The culture was centrifuged and the pellet was suspended in 5 ml of cold 50 mM $CaCl_2$. The suspension was placed on 0° C. for 40 minutes and then centrifuged. 0.25 ml of cold 50 mM $CaCl_2$ and 60 µl each of the recombinant plasmids as prepared in (4)(a) and (b) were added to the pellet in a separate tube. The mixture was incubated on ice for 40 minutes, heat-shocked at 42° C. for two minutes, placed on ice for five minutes, and added to 10 ml of 2×YT medium. The mixture was incubated at 37° C. for 90 minutes with shaking, then centrifuged. The pellet was suspended in 1 ml of 2×YT medium, and 10 µl of the suspension was plated on a 2×YT agar plate containing 50 µg/ml of ampicillin. The plate was incubated at 37° C. The colony grown on the plate was selected by the colony hybridization method: The colony was transferred to a nitrocellulose filter and lysed. The DNA fixed on the filter was hybridized to the probe as described in (2). The filter was autoradiographed and a recombinant colony was selected. Additionally, the presence of a nitrile hydratase gene in the transformant was confirmed according to the Southern hybridization method.

(6) Isolation and Purification of Recombinant Plasmid and Construction of the Restriction Map of the Inserted DNA Fragments The transformant selected as described in (5) was grown in 100 ml of a 2×YT medium containing 50 µg/ml of ampicillin at 37° C. overnight (12 hours). The bacterial cells were harvested and TNE was added to the cells. The cells were collected again by centrifugation, and 8 ml of STE and 10 mg of lysozyme were added to the cells. The mixture was incubated at 0° C. for five minutes. 4 ml of 0.25M EDTA, 2 ml of 10% SDS (at room temperature) and 5 ml of 5M NaCl were added to the mixture. The mixture was incubated at 0°–4° C. for three hours, and ultracentrifuged. ½ volume of 3.0% PEG 6000 was added to the supernatant. The mixture was incubated at 0°–4° C. overnight (12 hours) and centrifuged again. TNE was added to the pellet to bring the volume up to 7.5 ml. CsCl was added to the mixture. The mixture was centrifuged to rid of proteins. Then, 300–500 mg/ml of ethidium bromide was added to the supernatant and the mixture was transferred to a centrifuge tube. The tube was heat-sealed and ultracentrifuged. cccDNA was removed using a peristaltic pump. A bit more than equal volume of isopropyl alcohol saturated with water was added to cccDNA to remove ethidium bromide. The DNA sample was dialyzed against TE, resulting in about 3 ml of recombinant DNA. The recombinant plasmid containing a 4.6 kb DNA fragment was designated as pPCN1 (The recombinant plasmid containing a 4.7 kb DNA fragment was designated as pPCN3).

Figure 1:
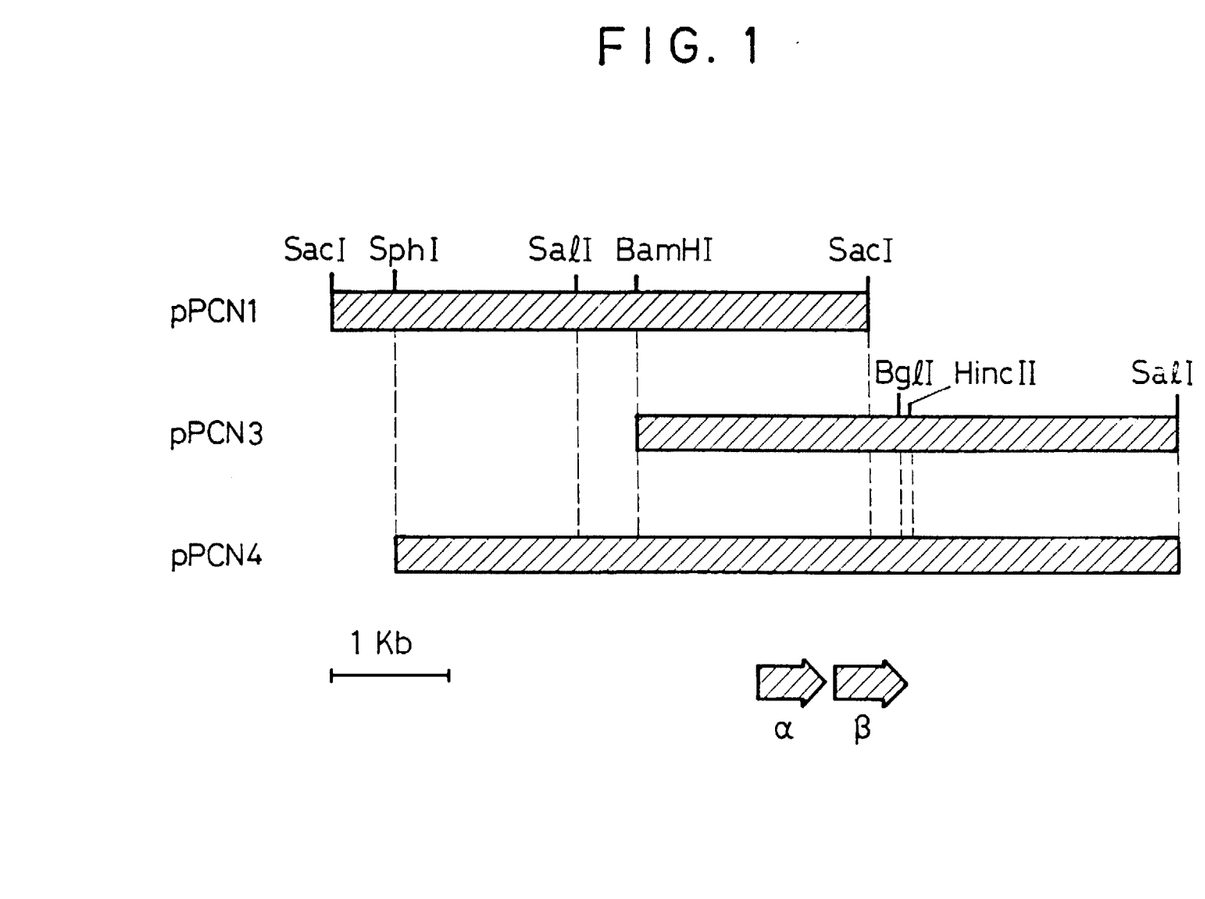
FIG. 1 shows restriction maps of recombinant plasmids, pPCN1, pPCN3 and-pPCN4.

These plasmid DNAs were digested with EcoRI, BamHI, PstI, SacI and SalI. The restriction maps were constructed and are shown in FIG. 1.

(7) DNA Sequencing

The location of a nitrile hydratase gene in the DNA fragments of pPCN1 and pPCN3 was determined according to the restriction map constructed and to the Southern hybridization method. Based on the results, the 2.456 kb BamHI-HincII DNA fragment was sequenced by the Sanger method [Sanger, F., Science 214: 1205–1210 (1981)] using M13 phage vector. The 2.456 kb DNA fragment from *Pseudomonas chlororaphis* B23 is shown in the Sequence Listing as defined by SEQ ID: No. 8.

All the nucleotide sequence deduced from the amino acid sequence as determined in (1) was found in the sequence as determined above. The sequence analysis also revealed that the DNA fragment contained the sequence coding for the α- and β-subunits.

(8) Insertion of the BamHI-HincII DNA Fragment into an Expression Vector and Transformation 2.2 kb SphI-BamHI fragment of pPCN1 and 4.7 kb BamHI-SalI fragment of pPCN3.were cleaved and both fragments were ligated (FIG. 1). The ligated fragment was inserted into the SphI-SalI site of an expression vector pUC19 and the construct was designated as pPCN4.

*E. coli* JM105 was transformed with pPCN4 in a similar manner as in (5) and the transformant was designated as JM105/pPCN4 (FERM BP-2779).

(9) Production of Nitrile Hydratase Using the Transformant and Conversion of Nitriles to Amides Using Nitrile Hydratase JM105/pPCN4 was inoculated into 10 ml of 2×YT medium containing 50 μg/ml of ampicillin and incubated at 26.5° C. overnight (12 hours). 100 μl of the resultant culture was added to 10 ml of 2×YT medium (50 μg/ml of ampicillin, 50 mg/l of $FeSO_4.7H_2O$, 10 mg/l of $MgSO_4.7H_2O$, 1 mg/l of pyrroloquinolinequinone). The mixture was incubated at 26.5° C. for five hours. IPTG was added to the mixture to a final concentration of 1 mM. The mixture was incubated at 26.5° C. for 10 hours. After harvesting the cells, the cells were suspended in 5 ml of 1/20M phosphate buffer (pH 7.7). 10 μl of the substrate solution (1M acrylonitrile) was added to 0.1 ml of the suspension. The mixture was incubated at 20° C. for 20 minutes. As a control, the mixture obtained by the same procedure as described above but from *E. coli* JM105 was used. The reaction mixture was tested for the presences of acrylamide (the product of the enzymatic reaction) and acrylonitrile using HPLC. Acrylamide but no acrylonitrile was found in the reaction mixture of JM105/pPCN4, whereas acrylonitrile but no acrylamide was found in the reaction mixture of JM105. A number of references are cited herein, the disclosures of which, in their entirities, are incorproated herein be reference.

---

What is claimed is:

1. An isolated DNA fragment encoding a polypeptide having nitrile hydratase activity, said polypeptide having an α-subunit as defined in the Sequence Listing by SEQ ID: No. 1 and a β-subunit as defined in the Sequence Listing by SEQ ID: No. 2, respectively.

2. An isolated DNA fragment, encoding a polypeptide having nitrile hydratase activity, which consists of the nucleotides 1021–2325 of SEQ ID: No. 8.

3. A plasmid pPCN4 obtainable from E. coli JM105/pPCN4 having Accession Number FERM BP-2779 which contains the DNA of claim 1.

4. A DNA comprising the DNA of claim 2 in a recombinant cloning vector.

5. A transformed cell containing plasmid pPCN4 obtainable from E. coli JM105/pPCN4 having Accession Number FERM BP-2779.

6. A transformed cell containing the recombinant DNA of claim 4.

7. A method of producing amides which comprises culturing the transformant as claimed in claim 4, and hydrating nitriles to amides using the resultant culture, isolated bacterial cells, the culture supernatant, or an extract of the culture, or a fixed material thereof.

8. A method of producing amides which comprises culturing the transformant as claimed in claim 6, and hydrating nitriles to amides using the resultant culture, isolated bacterial cells, the culture supernatant, or an extract of the culture, or a fixed material thereof.

* * * * *